United States Patent [19]

Williams

[11] 4,117,846
[45] Oct. 3, 1978

[54] SKIN CONDUCTING ELECTRODE AND ELECTRODE ASSEMBLY

[75] Inventor: Frank R. Williams, Utica, N.Y.

[73] Assignee: Consolidated Medical Equipment, Utica, N.Y.

[21] Appl. No.: 816,952

[22] Filed: Jul. 19, 1977

Related U.S. Application Data

[63] Continuation of Ser. No. 684,317, May 7, 1976, abandoned.

[51] Int. Cl.² .............................................. A61N 3/06
[52] U.S. Cl. ................................ 128/303.13; 128/417
[58] Field of Search .................... 128/303.13, 404, 410, 128/411, 416–418, 2.06 B, 2.1 R, DIG. 4

[56] References Cited

U.S. PATENT DOCUMENTS

| | | | |
|---|---|---|---|
| 1,973,387 | 9/1934 | Neymann et al. | 128/416 |
| 2,644,050 | 6/1953 | Seiger | 128/417 X |
| 3,720,209 | 3/1973 | Bolduc | 128/2.06 B |
| 3,817,252 | 6/1974 | Maurer | 128/416 |
| 3,841,312 | 10/1974 | Corasanti | 128/2.06 B |
| 3,976,055 | 8/1976 | Monter et al. | 128/2.06 B |

FOREIGN PATENT DOCUMENTS

| | | | |
|---|---|---|---|
| 122,258 | 2/1972 | Denmark | 128/206 B |
| 2,208,653 | 4/1973 | Fed. Rep. of Germany | 128/2.06 B |
| 2,239,596 | 2/1974 | Fed. Rep. of Germany | 128/416 |
| 353,189 | 10/1937 | Italy | 128/410 |

*Primary Examiner*—Lee S. Cohen
*Attorney, Agent, or Firm*—Larson, Taylor and Hinds

[57] ABSTRACT

A disposable skin conducting electrode assembly and electrode therefor for use on a patient wherein the electrode assembly comprises an electrolyte pad, an electrode and an adhesive pad. In one embodiment of the invention the electrode is a thin stainless steel plate having a periphery shaped to provide a plurality of recesses in the contour thereof and the adhesive pad is a solid sheet having greater overall length and width dimensions than the electrode. Thus the adhesive pad extends over the recesses in the periphery of the electrode and provides greater adhesive area for adhering the electrode assembly to the skin of the patient. An external conductor is connectable to a conductive, single piece, solid metal stud or post attached to the electrode extending through an orifice in the adhesive pad. A pair of washers are mounted on the stud on either side of the adhesive pad for mechanically retaining the stud and electrode in position.

5 Claims, 5 Drawing Figures

SKIN CONDUCTING ELECTRODE AND ELECTRODE ASSEMBLY

This is a continuation, of application Ser. No. 684,317 filed May 7, 1976, now abandoned.

FIELD OF THE INVENTION

This invention relates to a skin conducting electrode and electrode assembly. More specifically the present invention relates to a disposable skin conducting electrode and electrode assembly attachable to a patient for use as a return electrode during electrosurgery or for use as an active electrode for applying an electric current to a portion of a patient's body.

BACKGROUND OF THE INVENTION

Electrosurgery is the use of high frequency electrical current (usually radio frequencies of 1 to 5 megahertz) for cutting tissues and for also causing coagulation of hemostasis of tissues. It is also used as an exclusive technique in transurethral resections (TUR's) and laparoscopic tubal ligations. The basic mechanisms responsible for either the cutting or coagulation of the tissues is the production of heat either at the immediate site of the electrical arc or in adjacent tissue. This heat is the result of the unique properties of high frequency current with the current density and duration of current flow being recognized as determining the amount of heat generated in the tissue. Two basic wave forms are used: an undamped sinusoidal wave form found most useful for cutting tissue; and a series of highly damped sinusoidal waves found most effective in coagulating tissue. High frequencies are used in eletrosurgery because they will not stimulate the patient's muscles and they are easily coupled into the tissues.

Although many standards exist for electrosurgical units, the following have been proposed as appropriate approximations of the characteristics of electrosurgical units. The units are normally capable of delivering at least 150 watts of cutting power into 500 ohms of resistance. Coagulation power is at least 50 watts. The load impedance is normally in the range between 100 and 1000 ohms, the impedance varying depending upon the type of tissue (bone, skin, fat or muscle,) location, (surface or underlying tissue), and local blood circulation. The amount of current varies with the load impedance, whether cutting or coagulation is being done, and the type of surgery involved and can range from 2000 ma. for cutting TUR down to 240 ma. for general coagulation use. Electrosurgery is discussed in greater detail in volume 2 of "Health Devices", Issues Nos. 8–9, 11, and 12 (June-October 1973), a monthly publication by "Emergency Care Research Institute of Philadelphia, Pennsylvania."

Electrosurgery, like all other uses of electricity, requires a complete circuit for current to flow. The circuit begins at the high frequency generator, goes through an active cable and an active electrode to the patient (who constitutes the load) and returns to the generator by way of a grounding pad electrode and a cable attached therebetween. The ability of electrosurgical high frequency current to affect tissue depends on the current density, the greater the current density the greater the heating effect. If the electrode is small, the heating will be concentrated near the electrode's point of contact with a patient. Obviously this is desired with the active electrode in order to cause the cutting or coagulation of tissue. However, no tissue heating is desired near the point where the current leaves a patient to return to the electrosurgical unit. Thus the return electrode or grounding pad electrode should provide a low impedance and a low current density path for the return current. If the grounding pad electrode does not provide a low impedance path for the return current, the current will seek alternate means to return to the electrosurgical unit and complete the circuit. Usually the alternate paths provide high current density and tissue heating and burns on the patient are the likely result. Thus, good patient contact with a return electrode having very low current density is necessary to avoid the alternate current pathways. Similarly, burns can occur at the return electrode if there is inadequate patient contact with the electrode to disperse the current. Thus, the use of an adequate grounding pad electrode is necessary in order to assure safe, burn-free electrosurgery.

Most hazards of electrosurgical units involve failure of the electro-mechanical connection between the grounding pad electrode and electrosurgical units or inadequate patient contact with the grounding pad electrode. Grounding pad electrodes, therefore, should conform to the patient, resist patient scratching, and should have connectors that are rugged and able to withstand routine use.

Because the body has an extremely low impedance to surface current, the grounding pad electrode can be located almost anywhere on the body. Nevertheless, in general the larger the electrode, the flusher the electrode is to the skin, and the closer the electrode is placed to the operating site, the lower will be the amount of required electrosurgical power. Generally, the prior art electrodes are applied around a curved area (e.g., the arm or leg) or comprise a large metal plate that is placed beneath a large flat area of the patient (e.g., the back or buttocks). However, in many operations (such as a chest operation) the patient is placed on his side and the arms are used for blood transfusions and sampling and for a central vascular pressure monitor and the thighs may be used for connections to a heart lung machine. Thus there is very little area left on the patient on which to attach a conventional grounding pad electrode.

There are numerous electrodes in the prior art and those presently known to the applicant include the electrodes disclosed in the following U.S. patents: Patrick, U.S. Pat. No. 3,848,600; Johnson U.S. Pat. No. 3,830,229; Anderson U.S. Pat. No. 3,683,923; Estes U.S. Pat. No. 3,601,126; Bolduc U.S. Pat. No. 3,543,760; Bolduc U.S. Pat. No. 3,642,008; Bolduc U.S. Pat. No. 3,699,968; Bolduc U.S. Pat. No. 3,720,209; Sessions U.S. Pat. No. 3,741,219; Kawaguchi U.S. Pat. No. 3,685,645; Blackett U.S. Pat. No. 3,662,757; Smith U.S. Pat. No. 2,887,112; Consentino U.S. Pat. No. 3,580,240; Berman U.S. Pat. No. 3,085,577; Maurer U.S. Pat. No. 3,817,252; McDonald U.S. Pat. No. 3,386,445; Corasanti U.S. Pat. No. 3,841,312 and Sarbacher U.S. Pat. No. 3,472,233. In addition, the prior art is thoroughly discussed in the aforementioned "Health Devices" magazine.

The aforementioned electrodes can be divided into disposable and reusable electrodes. The reusable grounding pad electrodes usually comprise a large metal plate made from lead, aluminum, or stainless steel. These electrodes suffer from numerous disadvantages. These plates are usually very large and rigid because of their thickness and hence do not conform very well to the body contact area. In addition, because the body contact area can be rounded, bony or have irregular body surfaces, only a small contact area may be presented to the large electrode, thereby resulting in burns. In addition, the body contact area may be reduced by the layers of sheets or surgical drapes being caught between the metal grounding plate and the patient before and during the surgical procedure. Finally, the plates require the body weight for contact and therefore must be under the body. Because of the body contour, there are only a few possible body locations at which these plate electrodes can be used and the patient must usually be moved in order to place the electrode which may be difficult because of the patient's condition or weight. It may also be difficult to ensure that the patient is in good contact with the electrode and that the patient remains in good contact therewith despite deliberate repositioning of the patient during the operation. In addition, the large plate electrodes may not be usable with pediatric or geriatric patients or patients having bony promiences or inadequate weight.

Reusable solid metal grounding plate electrodes, in general, have other disadvantages. The electrodes may become distorted, bent, and cracked with frequent use and thus provide less effective contact with the patient which may result in burns. Often the corners of the electrode will curl if the electrode is dropped or the electrode can be bent and distorted upon normal insertion and removal from beneath the patient. Occasionally tissue necrosis has occurred if the patient lies on a reusable electrode that has a bent edge or corner, which causes great pressure over a small area. In addition, the reusable electrode must be sanitized after each use, are usually large and inconvenient to store, and are usually expensive.

There are also available numerous types of disposable grounding pad electrodes, generally classifiable into the "plate-type" and the "adhesive-type". The plate-type disposable return electrodes are usually made of cardboard with a conductive foil coating or laminate on either one or both sides of the cardboard. The additional expense of putting foil on both sides of the cardboard has been justified to eliminate the possibility that the single sided cardboard will be placed under the patient with the wrong side (i.e., the cardboard side) against the patient. The adhesive-type disposable grounding pad electrodes normally comprise a conductive surface surrounded by an adhesive material. These electrodes can be placed around an arm or a leg and depend on adhesive, rather than the weight of the patient to hold them in place.

Disadvantages of the plate-type disposable grounding pad electrodes include splitting of the conductive surface after the electrode has been bent, curling and delamination if the cardboard backed electrodes become wet, are subjective to being torn, and the requirement to use an electrosurgical gel in order to assure good electrical contact with the skin. In addition to the foregoing, the conventional adhesive- type grounding adhesive-type have a generally smaller contact area and those which do not totally seal on the patient have a tendency to become wrinkled if not properly applied, have a tendency to lose their adhesive ability as a result of contact with fluids on or near the patient or snagging of the electrode, and must be applied around a curved area in order to keep enough uniform inward pressure on the pad for even current distribution. Furthermore, the use of both type electrodes often requires considerable retraining of the personnel who apply the electrodes to ensure proper application of the electrodes to the patient.

Many of the adhesive-type disposable grounding pad electrodes are also provided with a gel pad that is located in contact with the metal electrode and is placed against the patient's skin so as to assure a better electrical contact. One such electrode is disclosed in the aforementioned Patrick et al U.S. Pat. No. 3,848,600. The gel pad 32 disclosed therein is a very thick pad that is exposed to the air along its outer edge, thus allowing gel evaporation during long surgical procedures. The evaporation problem is exacerbated by the heating of the pad caused by the operating current. Gel pad drying results in increased contact impedance which in turn results in a greater gel pad temperature which further dries out the gel pad, and so forth.

Other difficulties experienced with prior art grounding pad electrodes include chemical reactions with aluminum electrodes with the resultant release of heat or caustic products and problems with cable connection to the electrode. The latter problem occasionally results in either the connecting cable coming loose or the coupling post attached to the metal plate working loose or, in multipiece posts, coming apart. The cable connection to the electrode assembly must be designed so as to withstand the flexure and strains of normal use. Numerous prior art electrode assemblies comprise a multipiece connecting post that is held in contact with the electrode plate by friction. This type of contact can result in a greater electrical impedance and is subject to being worked loose.

SUMMARY OF THE INVENTION

The present invention overcomes these and other disadvantages disclosed in or apparent from the prior art. A skin conducting electrode and electrode assembly in accordance with the present invention provides a conveniently sized, inexpensive, disposable device with a novel adhesive pattern that is flexible, provides greater effective contact area and is usable on flat, cruved or irregular body surfaces. Also this invention provides a proportionately larger adhesive contact area, and is generally more impervious to fluid damage after being applied to a patient. The interface impedance of the present invention is approximately equivalent to a continuous electrode having the same overall length and width, but the present invention uses less electrode material thereby providing greater material economics.

In one embodiment of the present invention, the adhesive pad extends completely around the gel pad and utilizes a very thin gel pad completely sealing the gel pad when the electrode assembly of the present invention is applied to a patient. In further embodiments of the invention, improved reliability of the electrical connection is obtained with the use of a one-piece, electrically conductive stud or post that is welded or brazed or otherwise electrically and mechanically connected to the top surface of the metal electrode plate. Finally, in a further specific embodiment, the electrode assembly is given greater mechanical strength and resistance to separation by anchoring the metal stud to the adhesive pad with large non-conductive washers sandwiching the adhesive pad.

When an electrode assembly according to the present invention is appied to a patient, there is less possibility of injury to the patient through restricted circulation as a result of the fact that the present electrode assembly need not be placed around a limb, and in fact need not even be placed on a limb. As a result of the flexibility of the present electrode assembly and the greater adhesion area actually extending into the electrode plate recesses, the present assembly is less prone to wrinkling of the foil or the foil curling up and cutting the patient. The present electrode assembly easily conforms to the body surface and can be aplied over bony areas, flat areas, and circular areas in any direction with equal ease. Because the adhesive pad of the present electrode assembly completely covers both the electrode and the electrolyte, the electrolyte cannot dry out during prolonged use and the electrode is protected against physical damage. Furthermore, it is virtually impossible to place the present electrode assembly with the wrong side against the patient.

In addition to being used as a grounding pad electrode for electrosurgery, the present skin conducting electrode and electrode assembly can be used in electrotherapy for wound healing, in medical diathermy, in transcutaneous nerve stimulation and direct nerve stimulation, and in muscle stimulation.

A skin conducting electrode in accordance with the present invention comprises an elongated metal plate having a periphery shaped to provide a plurality of recesses in the contour thereof. A disposable skin conducting electrode assembly in accordance with the present invention comprises the aforementioned electrode in contact along one side thereof with an electrolyte composition and an adhesive pad in adhesive contact along one side with the other side of the electrode. The adhesive pad adheres the electrode assembly to the skin of a patient and extends over the recesses in the electrode and thereby provides additional adhesive area for adhering to the skin of a patient.

Other objectives, features, and advantages of the present invention are discussed in or are apparent from the description of the preferred embodiment of the invention found hereinbelow.

BRIEF DESCRIPTION OF THE DRAWING

FIG. 4 is a side elevational view, somewhat enlarged, of the connecting post or stud of the electrode assembly.

FIG. 5 is a cross-sectional elevational view taken along lines 5—5 of FIG. 3.

DESCRIPTION OF THE PREFERRED EMBODIMENT

Figure 1:
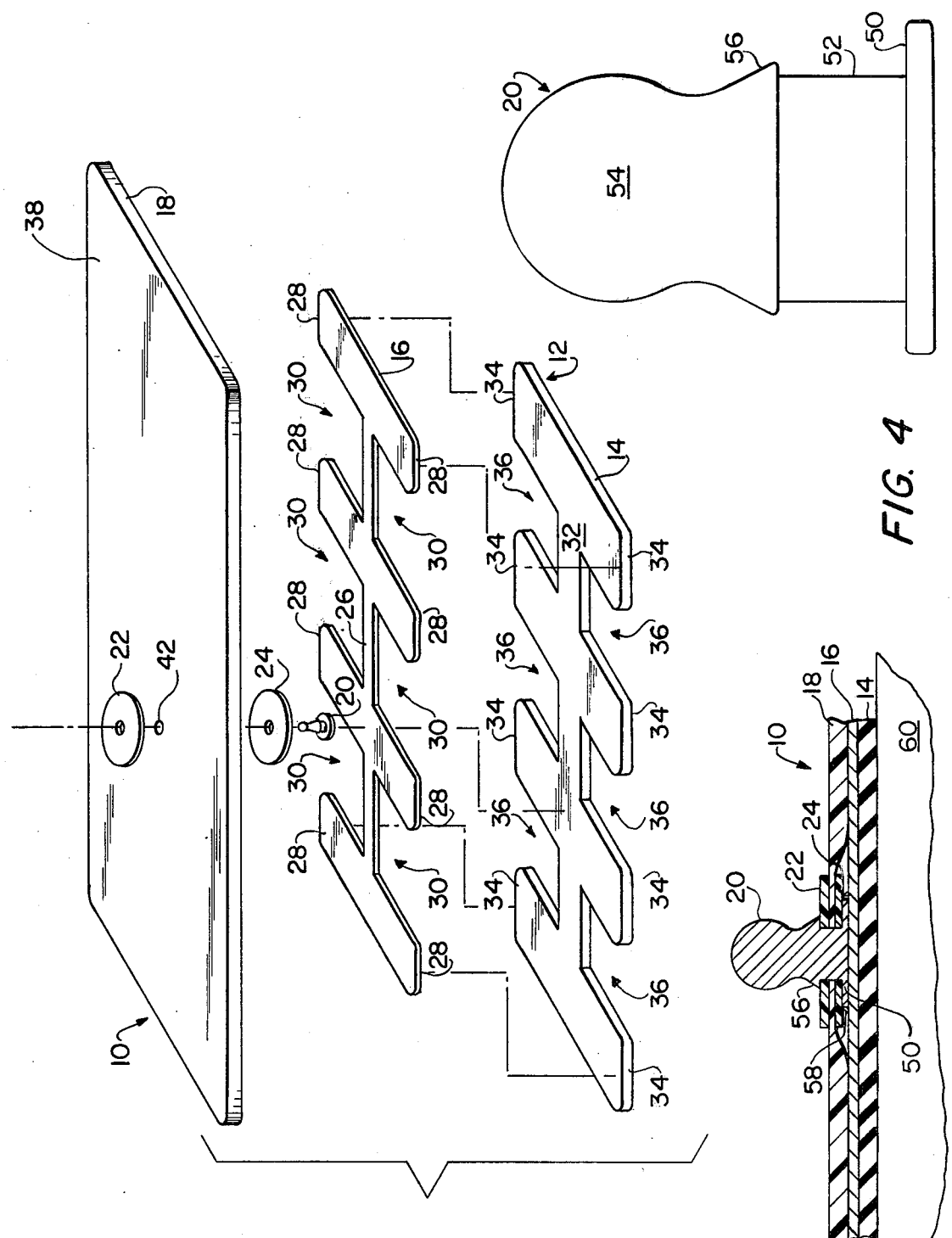
FIG. 1 is an exploded perspective view of the components of the skin conducting electrode assembly in accordance with the present invention.

It has been discovered that surface current readily disperses laterally across a patient's skin and that there is extremely low impedance to this lateral current dispersal. It has further been discovered that gaps or recesses can be provided in a conducting medium in electrical contact with the skin with almost negligible effect on the skin-conductor interface impedance. In addition, a negligible if any increase in electrical heating has been found. For example, if a ¾ inch square of material is removed from one side of a two inch square of conductor material, only a maximum of a few percent change of impedance has been observed. At the aforementioned electrosurgery radio frequencies (1 to 5 MHz) large recesses of up to 1 ½ to 2 inches in larger plates apparently produce little observed effect on interface impedance and electrode heating.

With reference to the figures in which like numerals represent like elements, an electrode assembly 10 is depicted which comprises an electrolyte composition 12 in a gel pad 14, an electrode 16 in contact along the bottom side thereof with the top side of gel pad 14, and a adhesive pad 18 in adhesive contact along the bottom side the reof with the top side of electrode 16. A metallic, one-piece post or stud 20 is fixedly mounted to the top surface of an electrode 16 in electrical contact therewith and upper and lower retaining washers 22 and 24 are located on either side of adhesive pad 18 and are rigidly mounted and retained on stud 20.

Figure 2:
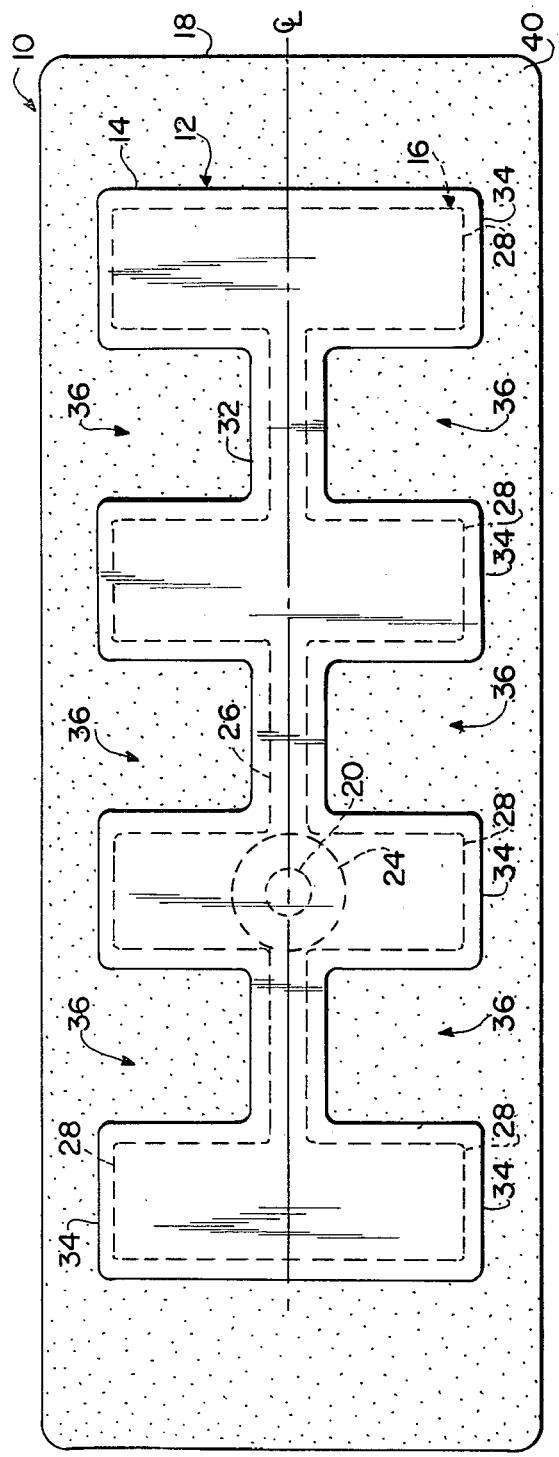
FIG. 2 is a bottom plan view of the electrode assembly showing the hidden components thereof in phantom.
Figure 3:
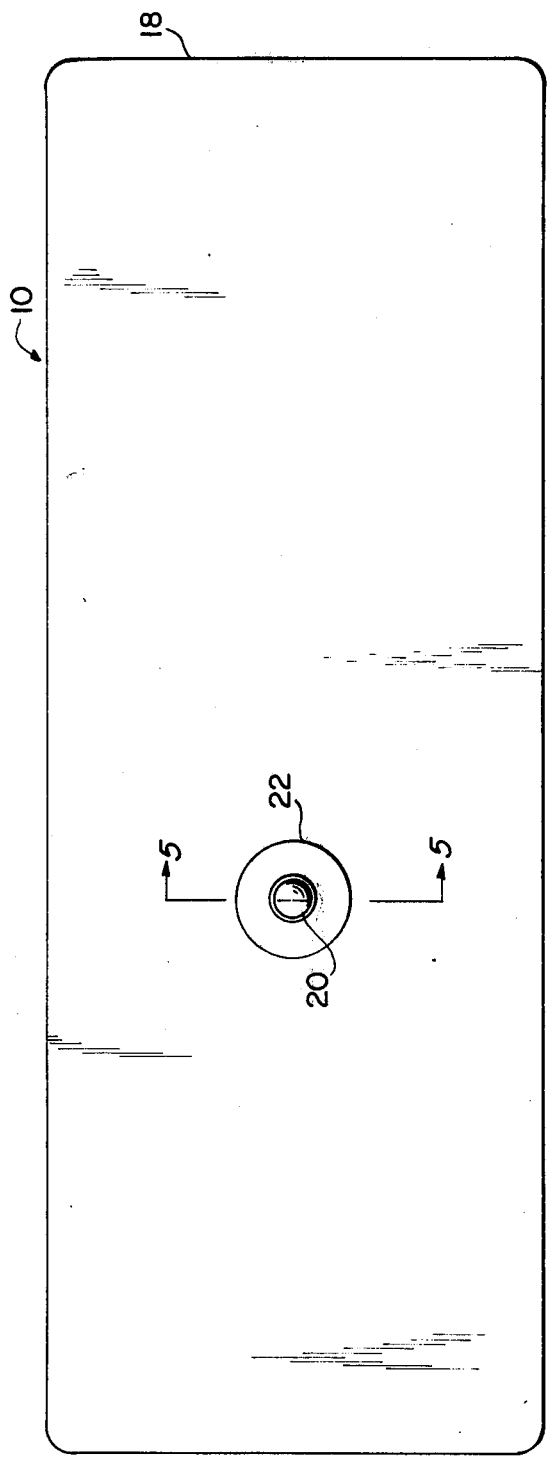
FIG. 3 is a top plan view of the present skin conducting electrode assembly.

As clearly shown in FIG. 1 and as shown in phantom in FIG. 2, electrode 16 is comprised of an overall rectangular shape with portions removed from either side. Viewed another way, electrode 16 comprises a main body portion 26 and a plurality of finger portions 28 integral with body portion 26 and extending outwardly in a transverse direction therefrom. In the embodiment disclosed in FIGS. 1 and 2, electrode 16 consists of 8 finger portions 28. Adjacent finger portions 28 define therebetween a recess 30 in the contour of electrode 16.

In one model made in accordance with the present invention, a satisfactory electrode was made from 316 stainless steel foil having a thickness of one thousandth of an inch. The model electrode had an overall length of 6¾ inches and an overall width of 2¼ inches. Finger portions 28 were constructed 2 inches on center at a width of ¾ of an inch thereby providing a recess having a longitudinal length of 1¼ inches. Body portion 26 had a transverse width of ¼ inch thereby providing recesses 30 with a transverse length of 1 inch. This particular electrode was found to have an interface impedance that was approximately equivalent, considering measuring difficulties and tolerances, as a rectangular electrode having overall dimensions of 6¾ inches by 2¼ inches. It was also found that material economies were afforded by having the "toothed-shape" of the electrode. This results by maufacturing the electrode from large sheet materials and interlacing the layouts of the electrodes and gel pads on the sheet materials. For manufacturing ease, each of the corners of electrode 16 have a ¼ inch radius. The elimination of sharp corners also helps to prevent the electrical field concentration points and the catching of finger portions 28 in other elements of electrode assembly 10.

Gel pad 14 has a correspondingly similar shape as electrode 16 and is comprised of a main body portion 32 and finger portions 34 integral therewith and extending in a transverse direction outwardly therefrom. Adjacent finger portions 34 define recesses 36. In the model of electrode assembly 10, gel pad 14 was made from one sixteenth inch thick 100 cpi "Scott Foam", a flexible cellular material, and was impregnated with an conductive electrolyte solution. As shown in FIG. 2, gel pad 14 is larger in each of the dimensions than electrode 16. In the aforementioned model of the invention, finger portions 34 of gel pad 14 were spaced 2 inches on center, had a width of 1 inch and defined a recess 36 having a longitudinal length of 1 inch. Body portion 32 has a transverse length of 0.500 inches and gel pad 14 has an overall length and width of 7 inches by 2½ inches. Thus, recess 36 has an overall transverse depth of approximately 1 inch.

Adhesive pad 18 has an upper, non-adhesive side 38 and a lower, adhesive side 40 and is provided with an orifice 42 completely therethrough. In the model of the invention, adhesive pad 18 was made from ⅛ eighth inch thick 4 pound "White Foam" cross link polyethylene material with an applied adhesive selected from a group of adhesives that are medically compatible and are well known to those of ordinary skill in the art. Adhesive pad 18 has a generally rectangular configuration with rounded corners so as to better ensure that the corners remain in adhesive contact when applied to a patient. In the aforementioned model of the invention, adhesive pad 18 had a length and width of 9 inches by 3¼ inches.

As shown in FIG. 2, adhesive pad is larger than both electrode 16 and gel pad 14 and extends over recesses 30 and 36 therein, respectively. In addition, adhesive pad 18 has an overall length and width larger than electrode 16 and gel pad 14 so as to extend beyond the overall periphery thereof. Thus electrode assembly 10 provides pockets for adhesive pad 18 to appear through the larger gel pad 14 which provides additional adhesive holding power of gel pad 14 against the skin of a patient under all conditions of skin contour for providing a better attachment of electrode assembly 10 to the patient during prolonged application and patient movement. Furthermore, the added adhesive areas provided in electrode assembly 10 maintan an intimate contact under contour and skin tension change conditions which in the past have caused the prior art electrodes to loosen the adhesive contact. Added advantages of the component configuration in electrode assembly 10 with the thin gel pad are that this configuration maintains an air tight seal entirely around the periphery of the gel pad and prevents the gel pad from drying out during use. The present electrode assembly 10 also can maintain a more positive attachment to a patient thereby providing a lower contact impedance, a cooler electrode, and one that can be placed closer to the operating site.

With reference to FIGS. 4 and 5, stud 20 consists of a solid, one-piece stainless steel or other conductive material element having a circular base 50, an upstanding pole portion 52 integral with base 50, and a helmet-shaped cap 54 integral with pole portion 52. At the juncture between cap 54 and pole portion 52, cap 54 has a flared out flange 56. By having stud 20 manufactured from a solid metal, no cavities can exist therein for possible contamination and the aforedescribed problems of multi-piece studs in the prior art are avoided. As shown at 58 in FIG. 5 stud 20 is welded, brazed or otherwise attached to the surface of electrode 16 thereby providing positive, reliable, electrical and mechanical contact therewith.

Improved mechanical strength of electrode assembly 10 is provided by having the dimension of pole portion 52 slightly less than the thickness of adhesive pad 18 thereby compressing and tightly retaining adhesive pad 18 between flange 56 and base 50 of stud 20 and hence to electrode 16. Alternatively, improved strength of electrode assembly 10 can be provided by retaining washers 22 and 24. As shown in FIGS. 1 and 5, lower retaining washer 24 is mounted on stud 20 and abuts base 50 thereof. Stud 20 extends through orifice 42 in adhesive pad 18 and upper retaining washer 22 is mounted on stud 20 above adhesive pad 18. Flange 56 of stud 20 securely holds the sandwich formed by the two retaining washers 22 and 24 and adhesive pad 18 together and on stud 20. Since stud 20 is also securely fastened to electrode 16, the two washers also have the effect of holding adhesive pad 18 to electrode 16. The anchoring of adhesive pad 18 to stud 20 and electrode 16 in the aforedescribed positive manners eliminates any danger of an accidental pulling out of stud 20 through inadvertent tugs on a grounding lead wire connected thereto during use.

In use, electrode assembly 10 is simply placed over the closest available site to the operating location and is pressed onto the skin 60 of the patient to adhere the adhesive of adhesive pad 18 thereto. It is usually standard practice to prepare the site where the grounding pad is to be located by first shaving the area and cleaning it with an antiseptic. A grounding wire (not shown) is then connected at one end to stud 20 and at the other end to the electrosurgery machine (also not shown).

Thus there has been described hereinabove a new and useful disposable skin conducting electrode assembly and electrode therefor for use on a patient undergoing electrosurgery or other electrical treatment. Because of the flexibility, yet relatively large effective area of the present electrode assembly 10, a skin conducting electrode is provided which has a very low interface impedance, less heat generation, can be securely attached to a patient, provides a positive electrical connection between the patient and the electrosurgery machine to complete the return path for the current, and permits the use of a lower operating power.

As mentioned above, a skin conducting electrode and electrode assembly according to the present invention can also be used for purposes other than a grounding pad electrode. When used as grounding pad electrode, the embodiments of the present invention are used as indifferent electrodes, but in the further aforementioned applications of the present invention, the electrode is used as an active electrode for applying an electrical current to the skin. In these further applications, the size and dimensions, as well as the external configuration, of the skin conducting electrode can vary.

When used in medical diathermy, also called endothermy, short wave diathermy, ultrasonic diathermy and medical thermopenetration, the present electrode is used for applying high frequency currents to the skin for the generation of heat in tissue as a result of the resistance offered by the tissue to the passage of the current. Although similar to electrosurgery, medical diathermy uses in practice larger electrodes for skin contact since the desired effect is only the generation of a heating or warming of muscles and tissues for therapeutic purposes and not for causing tissue destruction or blood coagulation. Medical diathermy is used extensively in physical therapy to produce muscle relaxation.

The present skin conducting electrode and electrode assembly can also be used for transcutaneous nerve stimulation. The "Gate therapy" of pain introduced the use of electrical currents in the treatment of chronic, irretractable or postsurgical pain. By placing skin conducting electrodes over appropriate areas and introducing currents having sufficient pulse widths and amplitude, pain impulses can be blocked or overridden, thereby alleviating the pain felt by the patient. In addition in many instances this type of stimulation also reduces or eliminates the need for extensive drug therapy and in other instances may be the only method for treatment of a patient's pain. In practice, medical treatment of pain associated with, for example, cancerous tumors, neurological disorders, chronic headaches, orthopedic disorders and the after effects of surgical trauma, can be accomplished by the transmission of an electrical impulse from a generator to between a pair of skin conducting electrodes positioned on the body in a configuration that directs the electrical impulse toward the "Gate" or susceptible point of a sensory nerve pathway. It is believed that the applied electrical impulse overrides or interferes with the transmission of the nerve pain impulse and hence eliminates or reduces the patient's perceived pain. The present invention is particularly applicable to transcutaneous nerve stimulation because a large gel area is needed to lower skin impedance so that skin burns can be prevented. The elongated and segmented configuration of the present electrode assembly 10 permits the use of electrode assembly 10 for treatment of immediate post-surgical pain since electrode assembly 10 can be placed parallel to and along the length of the surgical incision. In this manner, electrode assembly 10 can reduce the pain from surgical trauma and reduce the amount of pharmaceutical pain-killing drugs and limit the associated side effects of the drugs. Thus, the versatility provided by the present electrode assembly 10 permits the electrode assembly to be applied to almost any body area.

The present invention can also be used as an electrode for the transmission of an electrical impulse for directly stimulating a nerve or nerve pathway for restoring the physiological functions of a damaged nerve system. When used for wound healing, an electrode assembly according to the present invention can be used to apply an electrical current for enhancing or promoting the healing of traumatized, injured or displaced tissue. Long term application of high frequency current, and in some cases low voltage DC current can be accomplished with the present invention for aiding the healing of bedsores or decubitis ulcers, surgical incisions, skin ulcerations, and lacerations. Other wound healing applications can be used to aid the setting and proper healing of broken bones and fractured vertebrae, and even for treatment of curvature of the spine.

A further additional use of a electrode assembly according to the present invention is for muscle stimulation whereby electrical currents are applied to stimulate muscle activity as part of physical therapy that is needed because of nerve trauma or muscle injury or damage.

The present invention is usable for the additional aforementioned applications as a result of the ability of the present electrode assembly to efficiently conduct electrical impulses to the skin of a patient by allowing comformity of the electrode assembly to irregular body surfaces without affecting electrical conductivity and at the same time preventing tissue burn or adverse heating reaction.

Although the invention has been described in detail with respect to an exemplary embodiment thereof, it will be understood by those of ordinary skill in the art that variations and modifications may be effected within the scope and spirit of the invention.

I claim:

1. A skin conducting electrode assembly for use on a patient comprising, in combination, an electrode, said electrode comprising a thin conductive plate having a main body portion and a plurality of projections around the periphery of the main body portion to provide at least one recess in the contour thereof; means for making an electrical connection to said electrode; an adhesive pad in adhesive contact with one side of said electrode; a gel pad in contact with the other side of said electrode, said gel pad extending beyond the peripheral edges of the main body portion and the projections of the electrode, said adhesive pad extending over the at least one recess in the electrode and beyond the outer edges of the gel pad around the entire periphery thereof, the at least one recess between the projections being sufficiently large to insure that when the electrode assembly is placed in contact with a patient, the adhesive pad seals the assembly to the patient around the periphery thereof and within the at least one recess in the electrode to maintain the gel pad and electrode in firm contact with the skin and the gel pad covers the entire face and edges of the electrode to prevent direct contact of the electrode with the skin of the patient.

2. A skin conducting electrode assembly according to the claim 1 wherein said plurality of projections provide substantial conductive plate areas within the periphery of said projections.

3. A skin conducting electrode assembly for use on a patient comprising, in combination, an electrode, said electrode comprising a thin conductive plate having a main body portion and a plurality of projections around the periphery of the main body portion to provide a plurality of recesses in the contour thereof, the longitudinal distance across each of said recesses being at least as large as the longitudinal distance across each of said projections, means for making an electrical connection to said electrode, an adhesive pad in adhesive contact with one side of said electrode, a gel pad in contact with the other side of said electrode, said gel pad extending beyond the peripheral edges of the main body portion and projections of the electrode, said adhesive pad extending over the recesses in the electrode and beyond the outer edges of the gel pad around the entire periphery thereof whereby, when the electrode assembly is placed in contact with a patient, the adhesive pad seals the assembly to the patient around the entire periphery thereof and within the recesses in the electrode to maintain the gel pad and electrode in firm contact with the skin and the gel pad covers the entire face and edges of the electrode to prevent direct contact of the electrode with the skin of the patient.

4. A skin conducting electrode assembly as claimed in claim 3 wherein said adhesive pad has an aperture therein, and said electrical connection means comprising a conductive, one piece stud fixedly mounted on said electrode and extending through said aperture in said adhesive pad.

5. A skin conducting electrode assembly as claimed in claim 3 wherein said adhesive pad has an aperture therein, and said electrical connection means comprising a conductive, one piece stud fixedly mounted on said electrode, said stud terminating in a helmet shaped cap having an outwardly extending flange at the bottom, said stud extending through said aperture in said adhesive pad, a first retaining washer held on said stud beneath said outwardly extending flange and in contact with one side of said adhesive pad and a second retaining washer on said stud in contact with the other side of said adhesive pad.

* * * * *